US009345724B2

(12) United States Patent
Sherman et al.

(10) Patent No.: US 9,345,724 B2
(45) Date of Patent: *May 24, 2016

(54) SODIUM THIOSULFATE-CONTAINING PHARMACEUTICAL COMPOSITIONS

(71) Applicant: Hope Medical Enterprises, Inc., Scottsdale, AZ (US)

(72) Inventors: Craig Sherman, Scottsdale, AZ (US); Catherine Marie Smith, Grafton, WI (US); Kevin Robert Wirtz, Belgium, WI (US); Erich Schulze, Mission Viejo, CA (US)

(73) Assignee: Hope Medical Enterprises, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/310,133

(22) Filed: Jun. 20, 2014

(65) Prior Publication Data

US 2014/0302179 A1    Oct. 9, 2014

Related U.S. Application Data

(63) Continuation of application No. 14/222,766, filed on Mar. 24, 2014, now Pat. No. 9,144,580, which is a continuation of application No. 13/927,241, filed on Jun. 26, 2013, now Pat. No. 8,715,746, which is a continuation of application No. 12/831,331, filed on Jul. 7, 2010, now Pat. No. 8,496,973.

(60) Provisional application No. 61/223,993, filed on Jul. 8, 2009.

(51) Int. Cl.
| | | |
|---|---|---|
| *A61K 33/04* | (2006.01) | |
| *A61K 33/00* | (2006.01) | |
| *A61K 33/14* | (2006.01) | |
| *A61K 33/22* | (2006.01) | |
| *C01B 17/64* | (2006.01) | |
| *A61K 31/404* | (2006.01) | |
| *A61K 31/519* | (2006.01) | |
| *A61K 31/573* | (2006.01) | |
| *A61K 31/60* | (2006.01) | |
| *A61K 45/06* | (2006.01) | |

(52) U.S. Cl.
CPC .............. *A61K 33/04* (2013.01); *A61K 31/404* (2013.01); *A61K 31/519* (2013.01); *A61K 31/573* (2013.01); *A61K 31/60* (2013.01); *A61K 33/00* (2013.01); *A61K 45/06* (2013.01); *C01B 17/64* (2013.01); *Y10T 436/23* (2015.01)

(58) Field of Classification Search
CPC ....... A61K 33/04; A61K 33/00; A61K 33/14; A61K 33/22; C01B 17/64
See application file for complete search history.

(56) References Cited

U.S. PATENT DOCUMENTS

| | | | |
|---|---|---|---|
| 1,488,829 A | 4/1924 | Plumstead | |
| 2,032,699 A | 3/1936 | Hayes et al. | |
| 2,475,616 A | 7/1949 | Ingraham | |
| 2,763,531 A | 9/1956 | Levenson | |
| 2,933,377 A | 4/1960 | Doubt et al. | |
| 3,965,247 A | 6/1976 | Hecklinger et al. | |
| 4,105,754 A | 8/1978 | Swaine et al. | |
| 4,162,187 A | 7/1979 | Smith et al. | |
| 4,292,311 A | 9/1981 | Sarnoff | |
| 4,590,183 A | 5/1986 | Bailey | |
| H1126 H | 1/1993 | Pan et al. | |
| 6,007,777 A | 12/1999 | Purcell et al. | |
| 6,251,354 B1 | 6/2001 | Greenwell et al. | |
| 6,855,306 B2 | 2/2005 | Bortle et al. | |
| 6,884,440 B2 | 4/2005 | Choi et al. | |
| 8,496,973 B2 * | 7/2013 | Sherman et al. ............. 424/711 |
| 8,568,793 B2 * | 10/2013 | Sherman et al. ............. 424/718 |
| 8,715,746 B2 * | 5/2014 | Sherman et al. ............. 424/711 |
| 2003/0235571 A1 | 12/2003 | Gojon-Romanillos | |
| 2006/0177523 A1 | 8/2006 | Neuwelt et al. | |
| 2006/0276339 A1 | 12/2006 | Windsor et al. | |
| 2007/0239107 A1 | 10/2007 | Lundberg et al. | |
| 2008/0069779 A1 | 3/2008 | Tamarkin et al. | |

FOREIGN PATENT DOCUMENTS

| | | |
|---|---|---|
| GB | 500489 | 8/1937 |
| JP | 2003-104870 | 11/1973 |
| JP | 48-038557 | 9/2001 |
| JP | 2005-232014 | 9/2005 |
| WO | WO 01/80832 | 11/2001 |

(Continued)

OTHER PUBLICATIONS

ICH Harmonised Tripartite Guideline Impurities: Guideline for Residual Solvents Q3C(R3), Parent Guideline dated Jul. 17, 1997, (Revised PDE for THF and NMP dated Sep. 12, 2002 and Oct. 28, 2002, incorporated in Nov. 2005).*
U.S. Appl. No. 12/703,448, filed Feb. 10, 2010, Sherman et al.
GE—Water & Process Technologies Analytical Instruments—Sievers InnovOx—Laboratory TOC Analyzer—Fact Sheet (2008).
Aldrich, Handbook of Fine Chemicals, Sigma-Aldrich Co., entry and Specification Sheet for Sodium Thiosulfate (2010).
Merck, "Safety Data Sheet," pp. 1-7 (2006).
Schreiber et al., "Adsorption of dissolved organic matter onto activated carbon—the influence of temperature, absorption wavelength, and molecular size," *Water Research* 39(15):3449-3456 (2005).
ScienceLab.com, "Material Safety Data Sheet," pp. 1-4 (2008).

(Continued)

*Primary Examiner* — John Pak
*Assistant Examiner* — Nathan W Schlientz
(74) *Attorney, Agent, or Firm* — Jones Day

(57) ABSTRACT

Provided herein are pharmaceutically acceptable sodium thiosulfate and pharmaceutical compositions thereof. Also provided herein are methods for determining the total non-purgeable organic carbon in a sodium thiosulfate-containing sample. Further provided herein are methods for producing pharmaceutically acceptable sodium thiosulfate. Still further provided herein are methods of treatment comprising the administration of pharmaceutically acceptable sodium thiosulfate.

15 Claims, No Drawings

(56) References Cited

FOREIGN PATENT DOCUMENTS

| WO | WO 2005/004884 | 1/2005 |
|----|----------------|--------|
| WO | WO 2005/007173 | 1/2005 |
| WO | WO 2010/093746 | 8/2010 |

OTHER PUBLICATIONS

Muldoon et al., "Delayed Administration of Sodium Thiosulfate in Animal Models Reduces Platinum Ototoxicity without Reduction of Antitumor Activity," *Clinical Cancer Research* 6(1):309-315 (2000).
Araya et al., "Sodium Thiosulfate Treatment for Calcific Uremic Arteriolopathy in Children and Young Adults," *Clinical Journal of the American Society of Nephrology* 1(6):1161-1166 (2006).
Response to technical request from representative of Merck relating to sodium thiosulfate purity (Jun. 27-29, 2011).
United States Pharmacopeia (USP) 34, p. 4259 (2011).
"Offer of information" submitted to the Japanese Patent Office on Jun. 16, 2014 in connection with Japanese counterpart application No. JP 2012-51695 (English Translation).
List of References cited in "Offer of information" including JP language publications.
English Translation of Experimental transcript.
English Translation of Certificate of Analysis.
Japanese Pharmacopeia XVI, pp. 1417-1418 (2014).
Product catalogue of Kokusan Chemical Co., Ltd (Laboratory Chemicals vol. 18), published on Jul. 1, 2006.
Sievers®, 800 Series Total Organic Carbon Analyzer, Operation and Maintenance Manual, Ionics, 2004.
Daijuichi Kaisei Nippon Yakkyokuhou Kaisetsusho, 1988, Guide for the Japanese Pharmacopoeia, Eleventh Edition, p. C-1099-1103, Kabusikigaisha Hirokawa Shoten, Oct. 15, 1988 (English Translation).
Daijugo Kaisei Nippon Yakkyokuhou Kaisetsusho, 2006, Guide for the Japanese Pharmacopoeia, Fifteenth Edition), p. C-2476-2479, Kabusikigaisha Hirokawa Shoten, Jun. 2006 (English Translation).
Written Standard for sodium thiosulfate pentahydrate, 2008, Kishida Chemical Co., Ltd., Dec. 19, 2008 (English Translation).
Japanese Industrial Standards, 2006, sodium thiosulfate pentahydrate (reagent) JIS 8637: 2006 (English Translation).
On the Guidelines for Residual Solvents in Drug Products, 1998, Notification No. 307 of the Evaluation and Licensing Division dated Mar. 30, 1998, Evaluation and Licensing Division Manager, Pharmaceutical and Medical Safety Bureau, Ministry of Health and Welfare (English Translation).
Certificate of Experimental Results, 2015, Sojo University, Faculty of Pharmaceutical Sciences, Clinical Pharmaceutics, Research, Prfessor: Keishi Yamazaki, Ph.D., Feb. 25, 2015 (English Translation).
Kagaku Binran Oyo Kagakuhen, 1986, Chemical Handbook, Applied Chemistry, edited by the Chemical Society of Japan, Maruzen Co., Ltd., Oct. 15, 1986, p. 234-236 (English Translation).
Kagaku Daijiten 2, 1971, Chemical Unabridged Dictionary 2, (cut-down version), edited by Kagaku Daijiten Hensyu Iinkai (Editorial Board for Chemical Unabridged Dictionary), Kyoritsu Shuppan Co., Ltd., Feb. 5, 1971, p. 437-438 (English Translation).
Seibutsu Tokishin-Igaku•Seibutsugaku Eno Oyo, 1988, Biotoxin-Application to Medicine and Biology, edited by Kato Iwao, Japan Scientific Societies Press, first edition, Jun. 10, 1988, p. 192 (English Translation).
Meissner et al., 2006, "Sodium Thiosulfate as a Promising Therapeutic Option to Treat Calciphylaxis," *Dermatology* 212:373-376.
Gutierrez and Wetter, 2012, "Calcinosis cutis in autoimmune connective tissue diseases," *Dermatologic Therapy* 25:195-206.
Arabshahi et al., 2012, "Abatacept and Sodium Thiosulfate for Treatment of Recalcitrant Juvenile Dermatomyositis Complicated by Ulceration and Calcinosis," *J. Pediatr.* 160(3):520-522.
Wolf et al., 2008, "," *Arch. Dermatol.* 144(12):1560-1562.
Kadiyala et al., 2008, "Nephrogenic Sysstemic Fibrosis Associated with Gadodversetamide Exposure: Treatment with Sodium Thiosulfate," *Am. J. Kidney Dis.* 53:133-137.
Daijuichi Kaisei Nippon Yakkyokuhou Kaisetsusho, 1988, Guide for the Japanese Pharmacopoeia, Eleventh Edition, p. C-1099-1103, Kabusikigaisha Hirokawa Shoten, Oct. 15, 1988.
Daijugo Kaisei Nippon Yakkyokuhou Kaisetsusho, 2006, Guide for the Japanese Pharmacopoeia, Fifteenth Edition), p. C-2476-2479, Kabusikigaisha Hirokawa Shoten, Jun. 2006.
United States Pharmacopeia, 2007, 31, p. 3260, Sodium Thiosulfate, Nov. 2007.
European Pharmacopoeia, 2008, 6.0, p. 2927, Sodium Thiosulfate, Jan. 2008.
Certificate of Analysis of sodium thiosulfate, 2006, Merck & Co, Inc., Mar. 24, 2006.
Written Standard for sodium thiosulfate pentahydrate, 2008, Kishida Chemical Co., Ltd., Dec. 19, 2008.
Japanese Industrial Standards, 2006, sodium thiosulfate pentahydrate (reagent) JIS 8637: 2006.
On the Guidelines for Residual Solvents in Drug Products, 1998, Notification No. 307 of the Evaluation and Licensing Division dated Mar. 30, 1998, Evaluation and Licensing Division Manager, Pharmaceutical and Medical Safety Bureau, Ministry of Health and Welfare.
Certificate of Experimental Results, 2015, Sojo University, Faculty of Pharmaceutical Sciences, Clinical Pharmaceutics, Research, Prfessor: Keishi Yamazaki, Ph.D., Feb. 25, 2015.
Applicant-initiated Interview Summary, date of interview: Mar. 12, 2013, in connection with U.S. Appl. No. 12/831,331.
Kagaku Binran Oyo Kagakuhen, 1986, Chemical Handbook, Applied Chemistry, edited by The Chemical Society of Japan, Maruzen Co., Ltd., Oct. 15, 1986, p. 234-236.
Kagaku Daijiten 2, 1971, Chemical Unabridged Dictionary 2, (cut-down version), edited by Kagaku Daijiten Hensyu Iinkai (Editorial Board for Chemical Unabridged Dictionary), Kyoritsu Shuppan Co., Ltd., Feb. 5, 1971, p. 437-438.
Qian Lin, et al., 2008, Chemical Engineering Journal, vol. 139, 2008, p. 264-271.
Seibutsu Tokishin-Igaku•Seibutsugaku Eno Oyo, 1988, Biotoxin-Application to Medicine and Biology, edited by Kato Iwao, Japan Scientific Societies Press, first edition, Jun. 10, 1988, p. 192.

\* cited by examiner

SODIUM THIOSULFATE-CONTAINING PHARMACEUTICAL COMPOSITIONS

This application is a continuation of U.S. patent application Ser. No. 14/222,766, filed Mar. 24, 2014, currently pending, which is a continuation of U.S. patent application Ser. No. 13/927,241, filed Jun. 26, 2013, now U.S. Pat. No. 8,715,746, issued May 6, 2014, which is a continuation of U.S. patent application Ser. No. 12/831,331, filed Jul. 7, 2010, now U.S. Pat. No. 8,496,973, issued Jul. 30, 2013, which claims the benefit of U.S. Provisional Patent Application No. 61/223,993, filed Jul. 8, 2009, the entire contents of each of which are incorporated herein by reference.

FIELD

Provided herein are pharmaceutically acceptable sodium thiosulfate (such as sodium thiosulfate pentahydrate) and pharmaceutical compositions thereof. Also provided herein are methods for determining the total non-purgeable organic carbon in a sodium thiosulfate-containing sample. Further provided herein are methods for producing pharmaceutically acceptable sodium thiosulfate. Still further provided herein are methods of treatment comprising the administration of pharmaceutically acceptable sodium thiosulfate.

BACKGROUND

Sodium thiosulfate pentahydrate has numerous industrial applications including such uses as removing chlorine from solutions, bleaching paper pulp, and extracting silver from ores. It is also used as a fixer in photography, a mordant in dyeing and printing textiles, and a pharmaceutical ingredient. Even though thousands of metric tons of sodium thiosulfate pentahydrate are produced annually, only a few hundred kilograms are utilized pharmaceutically for the production of sodium thiosulfate injection as currently indicated as a treatment for cyanide poisoning or for the production of a lotion containing sodium thiosulfate pentahydrate for the treatment of tinea versicolor. It has been recently reported that sodium thiosulfate pentahydrate is an effective treatment for calciphylaxis (Ackermann et al., *Archives of Dermatology* 2007, 143(10): 1336-1337). It has also been reported that sodium thiosulfate pentahydrate is an effective treatment for vascular calcification (O'Neill, *Kidney International* 2008, 74(11): 1376-1378). It has been reported that sodium thiosulfate pentahydrate is an effective treatment to prevent platinum-induced ototoxicity and nephrotoxicity that is associated with the use of platinum-containing chemotherapeutic agents (Skinner, *Current Opinions in Oncology* 1995, 7(4): 310-315).

The manufacture of pharmaceutical products in the United States is regulated by the Food and Drug Administration (FDA). Since the passage of the Federal Food Drug and Cosmetic Act in 1938, the FDA has required new pharmaceutical products and their corresponding active ingredients to be manufactured in accordance with the exacting requirements of "pharmaceutical grade" Good Manufacturing Practices as detailed in the United States Code of Federal Regulations 21 CFR 211. Because of the relatively small quantity of sodium thiosulfate pentahydrate that is currently used to formulate pharmaceutical products, no raw material supplier presently manufactures sodium thiosulfate pentahydrate in accordance with "pharmaceutical grade" Good Manufacturing Practices.

In addition to regulating manufacturing practices, the FDA establishes stringent quality specifications for each new pharmaceutical product and its corresponding active ingredients. A pharmaceutical product is classified as "new" if it was introduced to the market after the passage of the Food Drug and Cosmetic Act in 1938. As mandated in this Act, the FDA requires a new pharmaceutical product and its active ingredients to be manufactured in accordance with "pharmaceutical grade" Good Manufacturing Practices and to meet applicable quality specifications. When the Food Drug and Cosmetic Act was enacted in 1938, pharmaceuticals that were already on the market were classified as "grandfathered drugs" and were permitted to remain on the market without formal FDA approval if the product and its labeling remain unchanged. Any change to the product or its labeling would cause the "grandfathered drug" to become a "new" drug that is subject to FDA-imposed regulations and quality standards. Currently available sodium thiosulfate pentahydrate injection that is labeled solely for use as a treatment of cyanide poisoning and sodium thiosulfate pentahydrate-containing lotion that is labeled solely for use as a treatment of tinea versicolor are "grandfathered medications". Consequently, the product formulations and corresponding quality specifications have remain unchanged for decades.

In anticipation of the receipt of a New Drug Application for a sodium thiosulfate pentahydrate-containing pharmaceutical product, the FDA recently announced that sodium thiosulfate pentahydrate raw material for a new pharmaceutical product must be manufactured in accordance with "pharmaceutical grade" Good Manufacturing Practices and must conform to a new set of quality specifications. This new set of quality specifications is more expansive and stringent than the existing quality specifications. Currently available sodium thiosulfate pentahydrate raw material does not meet the new set of FDA quality standards and is unsuitable for use in the formulation of a new pharmaceutical product. Consequently, there is a clear and unmet need for purified sodium thiosulfate pentahydrate raw material that is manufactured in accordance with "pharmaceutical grade" Good Manufacturing Practices and that meets the new set of quality specifications in order to translate recent sodium thiosulfate pentahydrate-related research discoveries into FDA-approved clinical therapies.

Another hurdle in developing pharmaceutical grade sodium thiosulfate pentahydrate is the lack of an effective analytical method to determine total non-purgeable organic carbon in a sodium thiosulfate pentahydrate-containing sample, which is one of the new FDA-imposed quality standards. The conventional method for total non-purgeable organic carbon determination requires that any inorganic carbon must be removed before measuring the organic carbon content in a sample. This is typically achieved by adding acid. At low pH, the inorganic carbon and volatile organic carbon are converted to carbon dioxide, which is then purged from the sample. The sample is then routed to a combustion chamber with a catalyst and a temperature of approximately 680° C. to convert any remaining non-purgeable (non-volatile) organic carbon to carbon dioxide. The quantity of carbon dioxide thus produced is then determined using an infrared detector. However, this conventional method cannot be used to analyze a sodium thiosulfate pentahydrate-containing sample. When exposed to acid, sodium thiosulfate pentahydrate degrades to sulfur which can precipitate during the analysis. Salt from sodium thiosulfate pentahydrate may also precipitate during the analysis. Precipitants can damage laboratory equipment and interfere with analysis. Therefore, there is also a need for an analytical method for determining total non-purgeable organic carbon in a sodium thiosulfate pentahydrate-containing sample.

SUMMARY OF THE DISCLOSURE

Provided herein is sodium thiosulfate which contains no greater than about 10 ppm of non-purgeable organic carbon (NPOC) (also known as non-volatile organic carbon). Also provided herein is sodium thiosulfate which contains no greater than about 0.01% by weight of carbonate. Also provided herein is sodium thiosulfate which contains no greater than about 0.05 ppm of mercury. Also provided herein is sodium thiosulfate which contains no greater than about 0.003% by weight of selenium. Also provided herein is sodium thiosulfate which contains no greater than about 2 ppm of aluminum. Further provided herein is sodium thiosulfate which contains no greater than about 10 ppm of non-purgeable organic carbon, no greater than about 0.01% by weight of carbonate, no greater than about 0.05 ppm of mercury, no greater than about 0.003% by weight of selenium, and no greater than about 2 ppm of aluminum.

Also provided herein are pharmaceutical compositions, which comprise sodium thiosulfate and a pharmaceutically acceptable excipient, wherein the sodium thiosulfate contains no greater than about 10 ppm of non-purgeable organic carbon and/or no greater than about 0.01% by weight of carbonate and/or no greater than about 0.05 ppm of mercury and/or no greater than about 0.003% by weight of selenium and/or no greater than about 2 ppm of aluminum.

Also provided herein are methods of determining the total non-purgeable organic carbon in a sodium thiosulfate-containing sample, which comprises the steps of: a) contacting the sample with a predetermined amount of an inorganic acid-containing aqueous solution to form an aqueous sample solution; b) removing precipitates from the aqueous sample solution; c) contacting the sample solution with a predetermined amount of an oxidizer; and d) converting the organic carbon in the sample solution into carbon dioxide under a supercritical water oxidation (SCWO) condition. In one embodiment, the final amount of the inorganic acid is no less than about 2% of the final volume of the sample solution or the final amount of the oxidizer is no less than about 20% of the final volume of the sample solution.

Also provided are methods for preparing the sodium thiosulfate provided herein, which comprise the steps of: a) contacting sodium sulfite with sulfur in a solvent to form a reaction mixture; b) filtering the reaction mixture to yield a solution; c) concentrating the solution; d) exposing the solution to activated carbon; e) filtering the solution with activated carbon; and f) crystallizing the sodium thiosulfate pentahydrate from the solution.

Also provided herein are methods for treating an acute poisoning, including, but not limited to, cyanide poisoning, which comprise administering to a subject having an acute poisoning a therapeutically effective amount of sodium thiosulfate provided herein.

Also provided herein are methods for treating or preventing a platinum-induced ototoxicity, such as that is associated with the use of cisplatin or other platinum-containing pharmaceutical agents, which comprise administering to a subject having or at risk for having a platinum-induced ototoxicity, such as that is associated with the use of cisplatin or other platinum-containing pharmaceutical agents, a therapeutically effective amount of sodium thiosulfate provided herein.

Also provided herein are methods for treating or preventing a platinum-induced nephrotoxicity, such as that associated with the use of cisplatin or other platinum-containing pharmaceutical agents, which comprise administering to a subject having or at risk for having a platinum-induced nephrotoxicity, such as that associated with the use of cisplatin or other platinum-containing pharmaceutical agents, a therapeutically effective amount of sodium thiosulfate provided herein.

Also provided herein are methods for treating a calciphylaxis which comprise administering to a subject having a calciphylaxis a therapeutically effective amount of sodium thiosulfate provided herein.

Also provided herein are methods for treating a vascular calcification, including by not limited to atherosclerosis, which comprise administering to a subject having a vascular calcification, including by not limited to atherosclerosis, a therapeutically effective amount of sodium thiosulfate provided herein.

Also provided herein are methods for treating a dermatological disease or a condition associated with the skin, including, but not limited to, bacterial infection of the skin, mycotic infection of the skin, viral infection of the skin, mycotic infection of the nails, bacterial infection of the nails, viral infection of the nails, mycotic infection of the nailbeds, bacterial infection of the nailbeds, viral infection of the nailbeds, psoriasis, scleroderma, inflammation of the skin, inflammation of the nails, and inflammation of the nailbeds, which comprise administering to a subject having a dermatological disease or a condition associated with the skin, a therapeutically effective amount of sodium thiosulfate provided herein.

DETAILED DESCRIPTION

To facilitate understanding of the disclosure set forth herein, a number of terms are defined below.

Generally, the nomenclature used herein and the laboratory procedures in inorganic chemistry, analytical chemistry, organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject. In one embodiment, the subject has or is at risk for a disease, disorder or condition provided herein. In another embodiment, the patient has or is at risk for a disease, disorder or condition wherein the disease, disorder or condition, or a symptom thereof, can be treated, prevented or ameliorated by the administration of sodium thiosulfate.

The term "host" refers to a unicellular or multicellular organism in which a virus can replicate, including, but not limited to, a cell, cell line, and animal, such as human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptom(s); barring a subject from acquiring a disease; or reducing a subject's risk of acquiring a disorder, disease, or condition.

The term "therapeutically effective amount" is meant to include the amount of a compound, such as sodium thiosulfate, that, when administered, is sufficient to treat or prevent development of, or alleviate to some extent, one or more of the symptoms of the disorder, disease, or condition being treated. The term "therapeutically effective amount" also refers to the amount of a compound, such as sodium thiosulfate, that is sufficient to elicit the biological or medical response of a cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid (e.g., water, such as deionized or sterile water) or solid filler, diluent, excipient, solvent, or encapsulating material. In one embodiment, each component is "pharmaceutically acceptable" in the sense of being compatible with the other ingredients of a pharmaceutical formulation, and suitable for use in contact with cells, tissues, or organs of humans and animals without excessive toxicity, irritation, allergic response, immunogenicity, or other problems or complications, commensurate with a reasonable benefit/risk ratio. See, *Remington: The Science and Practice of Pharmacy*, 21st Edition, Lippincott Williams & Wilkins Philadelphia, Pa., 2005; *Handbook of Pharmaceutical Excipients*, 5th Edition, Rowe et al., Eds., The Pharmaceutical Press and the American Pharmaceutical Association: 2005; and *Handbook of Pharmaceutical Additives*, 3rd Edition, Ash and Ash Eds., Gower Publishing Company: 2007; *Pharmaceutical Preformulation and Formulation*, Gibson Ed., CRC Press LLC: Boca Raton, Fla., 2004.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 5%, 4%, 3%, 2%, 1%, 0.5%, or 0.05% of a given value or range. In certain embodiments, it is contemplated that the values preceded by the term "about" or "approximately" are exact.

The terms "active pharmaceutical ingredient", "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active pharmaceutical ingredient", "active ingredient" and "active substance" may be an optically active isomer of a compound described herein. As used herein, "active pharmaceutical ingredient", "active ingredient", and "active substance" may be the anhydrous, the monohydrate, dihydrate, trihydrate, quatrahydrate, pentahydrate, or other hydrated forms of sodium thiosulfate.

The term "sodium thiosulfate" includes anhydrous, monohydrate, dihydrate, trihydrate, quatrahydrate, pentahydrate, and other hydrated forms of sodium thiosulfate. In one embodiment, the "sodium thiosulfate" referred to herein is sodium thiosulfate pentahydrate ($Na_2S_2O_3.5H_2O$). In another embodiment, the sodium thiosulfate is pharmaceutical grade. The term "pharmaceutical grade" as used herein with respect to sodium thiosulfate means that the sodium thiosulfate was manufactured according to Good Manufacturing Practices (GMP) as detailed in the United States Code of Federal Regulations 21 CFR 211 and meets one or more of the purity levels recited herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "anti-solvent" refers to a liquid that is added to a solvent to reduce the solubility of a compound in that solvent, resulting in precipitation of the compound.

The terms "non-purgeable organic carbon" ("NPOC") and "non-volatile organic carbon" ("NVOC") refer to organic carbon-based substances that are not volatile and are not purged from material when exposed to acid.

1. Sodium Thiosulfate

Provided herein are purified forms of sodium thiosulfate, such as sodium thiosulfate pentahydrate ($Na_2S_2O_3.5H_2O$). In one embodiment, provided herein is pharmaceutical grade sodium thiosulfate. In another embodiment, provided herein are forms of sodium thiosulfate meeting or exceeding one, more than one or all FDA standards for sodium thiosulfate for pharmaceutical use. In another embodiment, provided herein are forms of sodium thiosulfate that were manufactured according to Good Manufacturing Practices (GMP) as detailed in the United States Code of Federal Regulations 21 CFR 211.

In one embodiment, the sodium thiosulfate is solid.

In one embodiment, the appearance of the sodium thiosulfate is colorless crystals.

In one embodiment, the appearance of a 10% solution containing the sodium thiosulfate is clear and colorless.

In one embodiment, the sodium thiosulfate is odorless.

In one embodiment, the presence of sodium thiosulfate in a 10% solution containing sodium thiosulfate provided herein is identified by the discharge of yellow color after the addition of a few drops of iodine TS.

In one embodiment, the presence of sodium in sodium thiosulfate provided herein is confirmed according to Method 191 in USP XXXII (2009), which is incorporated by reference herein in its entirety.

In one embodiment, the presence of thiosulfate in sodium thiosulfate provided herein is confirmed according to Method 191 in USP XXXII (2009).

In one embodiment, the sodium thiosulfate pentahydrate provided herein contains no less than about 99% by weight and/or no greater than about 100.5% by weight of sodium thiosulfate calculated on the anhydrous basis. In certain embodiments, the amount of anhydrous sodium thiosulfate in the sodium thiosulfate pentahydrate provided herein is determined according to USP colorimetric assay (USP XXXII (2009)).

In one embodiment, the sodium thiosulfate pentahydrate provided herein contains no less than about 98% by weight and no greater than about 102% by weight of sodium thiosulfate on an anhydrous basis as measured by ion chromatography.

In one embodiment, the sodium thiosulfate pentahydrate provided herein contains no less than about 98% by weight and/or no greater than about 102% by weight of sodium thiosulfate calculated on the anhydrous basis. In certain embodiments, the amount of sodium thiosulfate anhydrous in the sodium thiosulfate pentahydrate provided herein is determined by an ion chromatography. In certain embodiments, the amount of anhydrous sodium thiosulfate in the sodium thiosulfate pentahydrate provided herein is determined by an ion chromatography with electrochemical conductivity detection as described herein.

In another embodiment, the sodium thiosulfate provided herein has a pH between about 6 to about 8 when measured in a 10% solution at 25° C. In certain embodiments, the pH of the sodium provided herein is measured using a pH meter. In certain embodiments, the pH of the sodium thiosulfate provided herein is determined according to Method 791 in USP XXXII (2009).

In yet another embodiment, the sodium thiosulfate provided herein has water content of about 32% to about 37% by weight. In certain embodiments, the water content in the sodium thiosulfate provided herein is determined by Karl Fischer method. In certain embodiments, the water content in the sodium thiosulfate provided herein is quantitated according to Method 921 in USP XXXII (2009).

In yet another embodiment, the heavy metal content in the sodium thiosulfate provided herein is no greater than about 10 ppm of a heavy metal. The heavy metal content in the sodium thiosulfate provided herein is determined according to Method 231 in USP XXXII (2009).

In yet another embodiment, the sodium thiosulfate provided herein contains no greater than about 0.01% by weight of carbonate. In certain embodiments, the amount of carbonate in the sodium thiosulfate provided herein is determined by contacting a sodium thiosulfate sample with an acid, such as phosphoric acid, to convert carbonate to carbon dioxide and determining the amount of the carbon dioxide using a non-dispersive infrared detector.

In yet another embodiment, the sodium thiosulfate provided herein contains no greater than about 0.005% by weight of insoluble matter. In certain embodiments, the amount of insoluble material in the sodium thiosulfate provided herein is determined by dissolving 10 grams of the sodium thiosulfate provided herein in 100 mL of water, the solution is heated to boiling for 1 hr, the solution is filtered, washed with hot water, dried, cooled in a desiccator, and weighed.

In yet another embodiment, the sodium thiosulfate provided herein contains no greater than about 200 ppm by weight of chloride. In certain embodiments, the chloride content in the sodium thiosulfate provided herein is determined according to Method 221 in USP XXXII (2009).

In yet another embodiment, the sodium thiosulfate provided herein contains no greater than about 0.002% by weight of iron. In certain embodiments, the iron content in the sodium thiosulfate provided herein is determined using inductively coupled plasma mass spectrometry (ICP-MS). In certain embodiments, the iron content in the sodium thiosulfate provided herein is determined using inductively coupled plasma-optical emission spectroscopy (ICP-OES). In certain embodiments, the iron content in the sodium thiosulfate provided herein is determined according to Method 241 in USP XXXII (2009).

In yet another embodiment, the sodium thiosulfate provided herein contains no greater than about 0.001% by weight of lead. In certain embodiments, the lead content in the sodium thiosulfate provided herein is determined according to Method 251 in USP XXXII (2009).

In yet another embodiment, the sodium thiosulfate provided herein contains no greater than about 0.01% by weight of calcium. In certain embodiments, the calcium content in the sodium thiosulfate provided herein is determined using ICP-MS. In certain embodiments, the calcium content in the sodium thiosulfate provided herein is determined using flame emission spectrometry (FES).

In yet another embodiment, the sodium thiosulfate provided herein causes no turbidity when ammonium oxalate test solution prepared according to USP XXXII (2009) is added to an aqueous solution containing sodium thiosulfate (e.g., one gram of sodium thiosulfate dissolved in 20 mL of water).

In yet another embodiment, the sodium thiosulfate provided herein contains no greater than about 0.005% by weight of potassium. In certain embodiments, the potassium content in the sodium thiosulfate provided herein is determined using ICP-MS. In certain embodiments, the potassium content in the sodium thiosulfate provided herein is determined using FES.

In yet another embodiment, the sodium thiosulfate provided herein contains no greater than about 0.05% by weight of sulfite, or no greater than about 0.1% by weight of sulfite. In certain embodiments, the sulfite content in the sodium thiosulfate provided herein is determined according to the method for the determination of sulfite in American Chemical Society, Reagent Chemicals, $10^{th}$ Edition, incorporated by reference herein in its entirety.

In yet another embodiment, the sodium thiosulfate provided herein contains no greater than about 0.05%, no greater than about 0.1%, no greater than about 0.25%, or no greater than about 0.5% by weight of sulfate (as $SO_4$). In certain embodiments, the sulfate content in the sodium thiosulfate provided herein is determined according to the method for the determination of sulfate in American Chemical Society, Reagent Chemicals, $10^{th}$ Edition.

In yet another embodiment, the sodium thiosulfate provided herein contains no greater than about 0.001% by weight of sulfide. In certain embodiments, the sulfide content in the sodium thiosulfate provided herein is determined by the addition of lead (II) nitrate using methods described herein.

In yet another embodiment, the sodium thiosulfate provided herein contains no greater than about 0.002% by weight of nitrogen compounds (as N). In certain embodiments, the nitrogen compounds (as N) content in the sodium thiosulfate provided herein is determined according to the method for the determination of nitrogen compounds in American Chemical Society, Reagent Chemicals, $10^{th}$ Edition.

In yet another embodiment, the sodium thiosulfate provided herein contains no greater than about 10 ppm, no greater than about 100 ppm, no greater than about 500 ppm, no greater than about 1000 ppm, or no greater than 5000 ppm of total volatile organic carbon. In certain embodiments, the sodium thiosulfate provided herein contains no greater than the specific limits set forth in ICH Q3C(R3) for organic volatile impurities or a particular solvent (e.g., ethanol), the disclosure of which is incorporated by references in its entirety. In certain embodiments, the content of organic volatile impurities is determined according to Method 467 in USP XXXII (2009).

In yet another embodiment, the sodium thiosulfate provided herein contains total NPOC of no greater than about 60 ppb, no greater than about 2.5 ppm, no greater than about 8 ppm, no greater than about 10 ppm, no greater than about 20 ppm, no greater than about 25 ppm, or no greater than about 50 ppm. In certain embodiments, the sodium thiosulfate provided herein contains total NPOC of no greater than about 12 ppm. In certain embodiments, the total NPOC in the sodium thiosulfate provided herein is determined using methods described herein. In certain embodiments, the total NPOC in the sodium thiosulfate provided herein is determined by a) contacting the sodium thiosulfate with a predetermined amount of an inorganic acid-containing aqueous solution to form an aqueous sample solution; b) removing precipitates from the aqueous sample solution; c) contacting the sample solution with a predetermined amount of an oxidizer; and d) converting the organic carbon in the sample solution into carbon dioxide under a supercritical water oxidation (SCWO) condition.

In yet another embodiment, the sodium thiosulfate provided herein contains no greater than about 0.05 ppm of mercury. In certain embodiments, the mercury content in the sodium thiosulfate provided herein is determined using ICP- MS. In certain embodiments, the mercury content in the sodium thiosulfate provided herein is determined using ICP-OES. In certain embodiments, the mercury content in the sodium thiosulfate provided herein is determined according to Method 261 in USP XXXII (2009).

In yet another embodiment, the sodium thiosulfate provided herein contains no greater than about 2 ppm of aluminum. In certain embodiments, the aluminum content in the sodium thiosulfate provided herein is determined using ICP-MS. In certain embodiments, the aluminum content in the sodium thiosulfate provided herein is determined using ICP-OES. In certain embodiments, the aluminum content in the sodium thiosulfate provided herein is determined according to Method 206 in USP XXXII (2009).

In yet another embodiment, the sodium thiosulfate provided herein contains no greater than about 3 ppm of arsenic. In certain embodiments, the arsenic content in the sodium thiosulfate provided herein is determined using ICP-MS. In certain embodiments, the arsenic content in the sodium thiosulfate provided herein is determined using ICP-OES. In certain embodiments, the arsenic content in the sodium thiosulfate provided herein is determined according to Method 211 in USP XXXII (2009).

In yet another embodiment, the sodium thiosulfate provided herein contains no greater than about 0.003% by weight of selenium. In certain embodiments, the selenium content in the sodium thiosulfate provided herein is determined using ICP-MS. In certain embodiments, the selenium content in the sodium thiosulfate provided herein is determined using ICP-OES. In certain embodiments, the selenium content in the sodium thiosulfate provided herein is determined according to Method 291 in USP XXXII (2009).

In yet another embodiment, the total aerobic count of microbial load in the sodium thiosulfate provided herein is no greater than about 100 Colony Forming Units per gram (CFU/g). The total aerobic count of microbial load in the sodium thiosulfate provided herein is quantitated according to Method 61 in USP XXXII (2009).

In yet another embodiment, the total yeast and mold count in the sodium thiosulfate provided herein is no greater than about 20 CFU/g. The total yeast and mold count in the sodium thiosulfate provided herein is quantitated according to Method 61 in USP XXXII (2009).

In yet another embodiment, the sodium thiosulfate provided herein contains no greater than about 0.02 Endotoxin Units per milligram (EU/mg), no greater than about 0.1 EU/mg, or no greater than about 0.25 EU/mg of bacterial endotoxins. The amount of bacterial endotoxins in the sodium thiosulfate provided herein is quantitated according to Method 85 in USP XXXII (2009).

In yet another embodiment, the sodium thiosulfate provided herein contains no greater than 0.01% of a residual anti-caking agent.

In yet another embodiment, the sodium thiosulfate provided herein is characterized by one or more of the following:
containing no less than about 99% by weight and/or no greater than about 100.5% by weight of sodium thiosulfate on an anhydrous basis determined according to USP colormimetric assay;
containing no less than about 98% by weight and/or no greater than about 102% by weight of sodium thiosulfate on an anhydrous basis determined according to ion chromatography assay;
having a pH between about 6 to about 8 when measured in a 10% solution at 25° C.;
having water content of about 32% to about 37% by weight;
having an appearance of colorless crystals;
having a clear and colorless appearance as a 10% solution;
having no odor;
having a positive identification test for sodium;
having a positive identification test for thiosulfate;
having no turbidy when mixed with ammonium oxalate TS;
having heavy metal content of no greater than about 10 ppm;
containing no greater than about 0.01% by weight of carbonate;
containing no greater than about 0.005% by weight of insoluble matter;
containing no greater than about 200 ppm of chloride;
containing no greater than about 0.001% by weight of sulfide;
containing no greater than about 0.05% or no greater than about 0.1% by weight of sulfite;
containing no greater than about 0.05%, no greater than about 0.1%, no greater than about 0.25%, or no greater than about 0.5% by weight of sulfate;
containing no greater than about 0.002% by weight of iron;
containing no greater than about 0.01% by weight of calcium;
containing no greater than about 0.005% by weight of potassium;
containing no greater than about 10 ppm, no greater than about 100 ppm, no greater than about 500 ppm, no greater than about 1000 ppm, or no greater than 5000 ppm of organic volatile impurities;
having total NPOC of no greater than 60 ppb, no greater than about 2.5 ppm, no greater than about 8 ppm, no greater than about 10 ppm, no greater than about 20 ppm, no greater than about 25 ppm, or no greater than about 50 ppm;
containing no greater than about 0.05 ppm of mercury;
containing no greater than about 2 ppm of aluminum;
containing no greater than about 3 ppm of arsenic;
containing no greater than 0.001% by weight of lead;
containing no greater than about 0.002% by weight of nitrogen compounds (as N);
containing no greater than about 0.003% by weight of selenium;
containing no greater than 0.01% of a residual anti-caking agent;
having a total aerobic count of microbial load of no greater than about 100 CFU/g;
having a total yeast and mold count of no greater than about 20 CFU/g; and
containing no greater than about 0.02 EU/mg, no greater than about 0.1 EU/mg, or no greater than about 0.25 EU/mg of bacterial endotoxins.

In still another embodiment, the sodium thiosulfate provided herein is characterized by one or more of the following:
containing no less than about 99% by weight and/or no greater than about 100.5% by weight of sodium thiosulfate on an anhydrous basis determined according to USP colormimetric assay;
containing no less than about 98% by weight and/or no greater than about 102% by weight of sodium thiosulfate on an anhydrous basis determined according to ion chromatography assay;
having a pH between about 6 to about 8 when measured in a 10% solution at 25° C.;
having water content of about 32% to about 37% by weight;
having an appearance of colorless crystals;
having a clear and colorless appearance as a 10% solution;

having no odor;

having a positive identification test for sodium;

having a positive identification test for thiosulfate;

having no turbidy when mixed with ammonium oxalate TS;

having heavy metal content of no greater than about 10 ppm;

containing no greater than about 0.01% by weight of carbonate;

containing no greater than about 0.005% by weight of insoluble matter;

containing no greater than about 200 ppm of chloride;

containing no greater than about 0.001% by weight of sulfide;

containing no greater than about 0.05% or no greater than about 0.1% by weight of sulfite;

containing no greater than about 0.05%, no greater than about 0.1%, no greater than about 0.25%, or no greater than about 0.5% by weight of sulfate;

containing no greater than about 0.002% by weight of iron;

containing no greater than about 0.01% by weight of calcium;

containing no greater than about 0.005% by weight of potassium;

containing no greater than about 10 ppm, no greater than about 100 ppm, no greater than about 500 ppm, no greater than about 1000 ppm, or no greater than 5000 ppm of organic volatile impurities;

having total NPOC of no greater than 60 ppb, no greater than about 2.5 ppm, no greater than about 8 ppm, no greater than about 10 ppm, no greater than about 20 ppm, no greater than about 25 ppm, or no greater than about 50 ppm;

containing no greater than about 0.05 ppm of mercury;

containing no greater than about 2 ppm of aluminum;

containing no greater than about 3 ppm of arsenic;

containing no greater than 0.001% by weight of lead;

containing no greater than about 0.002% by weight of nitrogen compounds (as N);

containing no greater than about 0.003% by weight of selenium;

having a total aerobic count of microbial load of no greater than about 100 CFU/g;

having a total yeast and mold count of no greater than about 20 CFU/g; and containing no greater than about 0.02 EU/mg, no greater than 0.1 EU/mg, or no greater than about 0.25 EU/mg of bacterial endotoxins.

In certain embodiments, where the sodium thiosulfate is described as "containing no greater than" a certain amount of a particular material, the sodium thiosulfate does not contain a detectable amount of the material.

2. Preparation of Sodium Thiosulfate

In one embodiment, provided herein is a method for preparing the sodium thiosulfate provided herein, which comprise the steps of: a) contacting sodium sulfite with sulfur in a solvent to form a reaction mixture; b) filtering the reaction mixture to yield a solution; c) concentrating the solution; d) exposing the solution to activated carbon; e) filtering the solution with activated carbon; and f) crystallizing the sodium thiosulfate from the solution.

Suitable solvents for use in the methods provided herein include, but are not limited to, water (including, but not limited to water, purified water, ultrapure water, deionized water, and water for injection), methanol, ethanol, isopropanol (IPA), 1-propanol, 2-methoxyethanol, 2-ethoxyethanol, ethyleneglycol, acetone, N,N-dimethylformamide (DMF), N,N-dimethylacetamide, acetonitrile (ACN), dimethyl sulfoxide (DMSO), N-methyl pyrrolindone, tetrahydrofuran (THF), dioxane, acetic acid, trichloroacetic acid, trifluoroacetic acid, and a mixture thereof. In one embodiment, the solvent is aqueous. In another embodiment, the solvent is water. In yet another embodiment, the solvent is a mixture of water with a water-miscible solvent, including, but not limited to, methanol, ethanol, isopropanol (IPA), 1-propanol, 2-methoxyethanol, 2-ethoxyethanol, ethyleneglycol, acetone, N,N-dimethylformamide (DMF), N,N-dimethylacetamide, acetonitrile (ACN), dimethyl sulfoxide (DMSO), N-methyl pyrrolindone, tetrahydrofuran (THF), dioxane, acetic acid, trichloroacetic acid, trifluoroacetic acid, and a mixture thereof. In one embodiment, the solvent is water.

In certain embodiments, the mole ratio of the sulfur to the sodium sulfite in the contacting step is from about 0.5 to about 5, from about 1 to about 4, from about 1 to about 3, from about 1 to about 2, or from about 1.2 to about 1.6. In one embodiment, the ratio of the sulfur to the sodium sulfite in the contacting step is about 1.5.

In certain embodiments, the concentration of the sodium sulfite in the contacting step is from about 0.1 to about 100 M, from about 1 to about 10 M, from about 1 to about 5 M, from about 1 to about 4 M, from about 1 to about 3 M, from about 1 to about 2 M, from about 1.2 to about 1.8 M, or from about 1.3 to about 1.6 M. In certain embodiments, the concentration of the sodium sulfite in the contacting step is from about 1.3 to about 1.5 M.

In certain embodiments, the contacting step is carried out at a temperature ranging from about 40 to about 150° C., from about 70 to about 120° C., from about 90 to about 110° C., from about 90 to about 10° C., or from about 95 to about 100° C. In one embodiment, the temperature in the contacting step is from about 90 to about 100° C. In another embodiment, the temperature in the contacting step is from about 95 to about 100° C. In still another embodiment, the temperature in the contacting step is about 97° C.

In certain embodiments, the contacting step is carried out at a predetermined pH of no less than 13, no less than 12, no less than 11, no less than 10, no less than 9, no less than 8, or no less than 7. In certain embodiments, the predetermined pH is from about 6 to about 11, from about 6.5 to about 10.5, from about 7 to about 10, from about 7 to about 9, from about 7 to about 8.5, or from about 7 to about 8. In certain embodiments, a base is added to the reaction mixture in the contacting step to adjust to the predetermined pH. In certain embodiments, the base is an inorganic base. In certain embodiments, the base is sodium hydroxide.

In certain embodiments, a filtration step is carried out at a temperature ranging from about 5 to 100° C., from about 10 to about 50° C., from about 15 to about 40° C., from about 20 to about 30° C., or from about 20 to about 35° C. In certain embodiments, the filtration step is carried out at room temperature (about 21° C.).

In certain embodiments, a concentration step is performed by solvent evaporation, which comprises concentrating the filtered solution to produce a concentrated solution. In certain embodiments, the filtered solution is concentrated to a specific gravity ranging from about 1.20 to about 1.70, from about 1.30 to about 1.60, or from about 1.40 to about 1.50, or from about 1.40 to about 1.45. In certain embodiments, the concentration step is performed at a temperature ranging from about 5 to 100° C., from about 20 to about 80° C., from about 30 to about 70° C., from about 40 to about 60° C., or from about 45 to about 55. In certain embodiments, the concentration step is performed at about 50° C. In certain embodiments, the concentration step is performed under vacuum. In certain embodiments, the concentration step is performed from about 100 to about 755 mm Hg, from 300 to about 750 mm Hg, from 500 to about 750 mm Hg, from 600 to about 740 mm Hg, or from 700 to about 730 mm Hg. In certain embodiments, the concentration step is performed from 700 to about 730 mm Hg.

In certain embodiments, the concentrated solution is mixed with activated carbon of about 0.020 to 0.251% on a weight/weight basis for about 30 to 47 minutes at about 50° C. In certain embodiments, the activated carbon step is performed with not less than 0.025% activated carbon on a weight/weight basis for not less than 30 minutes at about 50° C.

In certain embodiments, the solution with activated carbon is refiltered at a temperature from about 20 to 55° C., or from about 40 to about 55° C. In certain embodiments, the refiltration step is performed at about 50° C.

In certain embodiment, the sodium thiosulfate pentahydrate is crystallized out from the concentrated, refiltered solution using conventional methods, including, but not limited to, cooling, chilling, solvent evaporation, addition of an anti-solvent, or reverse addition to an anti-solvent.

To accelerate the crystallization, the crystallization step may further comprise the step of seeding the filtered solution. The crystallization step may also comprise an isolation step, in which the precipitate may be isolated by a conventional method, such as filtration and centrifugation, followed by washing with a solvent and then drying.

Other methods known in the art may also be applicable for preparing the pharmaceutically acceptable sodium thiosulfate provided herein, including spray drying, roller drying, lyophilization, and melt crystallization.

3. Methods of Characterization: Determining the Total Non-Purgeable Organic Carbon in Sodium Thiosulfate Provided herein are methods of determining the total non-purgeable organic carbon in a sodium thiosulfate-containing sample, which comprise the steps of: a) contacting the sample with a predetermined amount of an inorganic acid-containing aqueous solution to form an aqueous sample solution; b) removing precipitates from the aqueous sample solution; c) contacting the sample solution with a predetermined amount of an oxidizer; and d) converting the organic carbon in the sample solution into carbon dioxide under a supercritical water oxidation (SCWO) condition. In one embodiment, the final amount of the inorganic acid is no less than about 2% of the final volume of the sample solution or the final amount of the oxidizer is no less than about 20% of the final volume of the sample solution.

In one embodiment, the inorganic acid is phosphoric acid. In another embodiment, the inorganic acid is 6 N phosphoric acid. In yet another embodiment, the final amount of the inorganic acid is no less than about 2% and no greater than about 50% of the final volume of the sample solution. In yet another embodiment, the final amount of the inorganic acid is about 2%, about 3%, about 4%, about 5%, about 6%, about 7%, about 8%, about 9%, about 10%, about 15%, about 20%, about 30%, about 40%, or about 50% of the final volume of the sample solution. In yet another embodiment, the final amount of the inorganic acid is about 6% of the final volume of the sample solution. In still another embodiment, the inorganic acid is 6 N phosphoric acid and the final amount of the inorganic acid is about 6% of the final volume of the sample solution.

The precipitates in the aqueous sample solution, if any, can be readily removed from the sample solution by methods known to one of skill in the art. In certain embodiments, the precipitates are removed from the sample solution by filtration. In certain embodiments, the precipitates are removed from the sample solution by centrifugation.

In one embodiment, the oxidizer is sodium persulfate. In another embodiment, the oxidizer is a 30% sodium persulfate solution. In yet another embodiment, the final amount of the oxidizer is no less than about 20% but no greater than about 90% of the final volume of the sample solution. In yet another embodiment, the final amount of the oxidizer is about 20%, about 25%, about 30%, about 35%, about 40%, about 45%, about 50%, about 55%, about 60%, about 65%, about 70%, about 75%, about 80%, or about 90% of the final volume of the sample solution. In yet another embodiment, the final amount of the oxidizer is about 45% of the final volume of the sample solution. In still another embodiment, the oxidizer is 30% sodium persulfate solution and the final amount of oxidizer is about 45% of the final volume of the sample solution.

In certain embodiments, the organic carbon in the sodium thiosulfate-containing sample is oxidized according any SCWO processes known in the art, such as those disclosed in U.S. Pat. Nos. 2,944,396, 4,543,190, 5,387,398, 5,405,533, 5,501,799, 5,560,822, 5,804,066, 6,054,057, 6,056,883, 6,238,568, 6,519,926, 6,576,185, 6,709,602, and 6,773,581, the disclosure of each of which is incorporated herein by reference in its entirety. In certain embodiments, the SCWO process is carried out in an InnovOx laboratory TOC Analyzer (GE Analytical Instruments, Inc., Boulder, Colo.). SCWO processes take advantage of the unique properties of water at conditions near and beyond the thermodynamic critical point of water (i.e., 375° C. and 218 atm). The increased pressure under supercritical water oxidation conditions dramatically increases the efficiency of the oxidation process by converting the organic carbon in the sodium thiosulfate-containing sample into carbon dioxide.

In certain embodiments, the sodium thiosulfate-containing sample solution is prepared by adding 5.0 g of a sodium thiosulfate-containing sample into water to make 100 mL solution. In certain embodiments, the water used in the method has total organic carbon of no greater than 0.10 ppm.

In certain embodiments, the method further comprises the step of determining the amount of carbon dioxide formed after oxidation. In certain embodiments, the carbon dioxide is quantitated using an infrared detector. In certain embodiments, the carbon dioxide is quantitated using a nondispersive infrared detector.

4. Pharmaceutical Compositions

Provided herein are pharmaceutical compositions comprising the sodium thiosulfate provided herein as an active ingredient, alone or in combination with a pharmaceutically acceptable vehicle, carrier, diluent, or excipient, or a mixture thereof.

The sodium thiosulfate provided herein may be administered alone, or in combination with one or more other active ingredients. The pharmaceutical compositions that comprise the sodium thiosulfate provided herein may be formulated in various dosage forms for oral, parenteral, and topical administration. The pharmaceutical compositions may also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration, which comprise the sodium thiosulfate provided herein, and one or more pharmaceutically acceptable excipients or carriers.

In another embodiment, the pharmaceutical compositions are provided in a dosage form for parenteral administration, which comprise the sodium thiosulfate provided herein, and one or more pharmaceutically acceptable excipients or carriers.

In yet another embodiment, the pharmaceutical compositions are provided in a dosage form for topical administration, including pulmonary administration, which comprise the sodium thiosulfate provided herein, and one or more pharmaceutically acceptable excipients or carriers.

In one embodiment, the pharmaceutical composition comprises sodium thiosulfate provided herein and water. In another embodiment, the pharmaceutical composition comprises from about 1 gram to about 100 grams, about 1 gram to about 75 grams, about 1 gram to about 50 grams, about 1 gram to about 25 grams or about 1 gram to about 12.5 grams of sodium thiosulfate provided herein in about 1 mL to about 1000 mL, about 1 mL to about 750 mL, about 1 mL to about 500 mL, about 1 mL to about 250 mL about 1 mL to about 100 mL, about 1 mL to about 50 mL or about 1 mL to about 25 mL of water. In another embodiment, the pharmaceutical composition comprises about 5 grams, about 10 grams, about 12.5 grams, about 15 grams, about 20 grams, about 25 grams, about 30 grams, about 50 grams, about 75 grams or about 100 grams or more of sodium thiosulfate provided herein in about 25 mL, about 50 mL, about 100 mL, about 250 mL, about 500 mL, about 750 mL or about 1000 mL or more of water.

In one embodiment, the pharmaceutical composition comprises sodium thiosulfate provided herein, one or more isotonic agents and one or more pH adjusting agents. In another embodiment, the pharmaceutical composition comprises sodium thiosulfate provided herein, one or more isotonic agents, one or more buffering agents and one or more pH adjusting agents. In a particular embodiment, the pharmaceutical composition comprises sodium thiosulfate provided herein, potassium chloride, boric acid and sodium hydroxide. In a specific embodiment, the pharmaceutical composition comprises sodium thiosulfate provided herein, potassium chloride, boric acid, sodium hydroxide and water (e.g., water for injection).

In one embodiment, the pharmaceutical composition comprises sodium thiosulfate provided herein and salicylic acid. In another embodiment, the pharmaceutical composition comprises about 5 to about 50%, about 10 to about 40%, about 15 to about 30% or about 20 to about 25% of sodium thiosulfate provided herein and about 0.1 to about 2%, about 0.1 to about 1.5%, about 0.5 to about 1.5%, about 0.5 to about 1.25% or about 0.5 to about 1% salicylic acid in a lotion. In another embodiment, the pharmaceutical composition comprises about 10%, about 15%, about 20%, about 25%, about 30% about 35% or about 40% or more of sodium thiosulfate provided herein and about 0.5%, about 0.75%, about 1%, about 1.25%, about 1.5% or about 2% salicylic acid in a lotion.

The pharmaceutical compositions provided herein may be provided in a unit-dosage form or multiple-dosage form. A unit-dosage form, as used herein, refers to a physically discrete unit suitable for administration to a human and animal subject, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, syringe, and individually packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

4.1. Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of nonaqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

4.2. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents (e.g., including, but not limited to, potassium chloride, mannitol, sodium chloride, dextran and glucose), buffering agents, antioxidants, local anesthetics, suspending and dispersing agents, wetting or emulsifying agents, complexing agents, sequestering or chelating agents, cryoprotectants, lyoprotectants, thickening agents, pH adjusting agents (e.g., including, but not limited to, an acid, such as boric acid or a base, such as sodium hydroxide), and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semisolid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions to diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

4.3. Topical Administration

The pharmaceutical compositions provided herein may be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy,* supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy,* supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

4.4. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

4.4.1. Matrix Controlled Release Devices

The pharmaceutical compositions provided herein in a modified release dosage form may be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers, and hydrophilic polymers, such as ethyl cellulose, cellulose acetate, crospovidone, and cross-linked partially hydrolyzed polyvinyl acetate, and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form may be prepared by methods known to those skilled in the art, including direct compression, dry or wet granulation followed by compression, melt-granulation followed by compression.

4.4.2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly (acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

4.4.3. Multiparticulate Controlled Release Devices

The pharmaceutical compositions provided herein in a modified release dosage form may be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates may be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4.4.4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

5. Methods of Use

In one embodiment, provided herein are methods for treating known or suspected cyanide poisoning, which comprise administering to a subject having or at risk for having cyanide poisoning, a therapeutically effective amount of sodium thiosulfate provided herein. In one embodiment, the subject is a mammal. In another embodiment, the subject is a human.

In one embodiment, provided herein are methods for treating or preventing platinum-induced ototoxicity, such as that associated with the use of cisplatin or other platinum-containing medication, which comprise administering to a subject having or at risk for having platinum-induced ototoxicity, such as that associated with the use of cisplatin or other platinum-containing medication, a therapeutically effective amount of sodium thiosulfate provided herein. In one embodiment, the subject is a mammal. In another embodiment, the subject is a human.

In another embodiment, provided herein are methods for treating or preventing platinum-induced nephtotoxicity, such as that associated with the use of cisplatin or other platinum-containing medication, which comprise administering to a subject having or at risk for having platinum-induced nephtotoxicity, such as that associated with the use of cisplatin or other platinum-containing medication, a therapeutically effective amount of sodium thiosulfate provided herein. In one embodiment, the subject is a mammal. In another embodiment, the subject is a human.

In yet another embodiment, provided herein are methods for treating a vascular calcification, including by not limited to atherosclerosis, which comprise administering to a subject having a vascular calcification, including by not limited to atherosclerosis, a therapeutically effective amount of sodium thiosulfate provided herein. In one embodiment, the subject is a mammal. In another embodiment, the subject is a human.

In certain embodiments, provided here are methods for treating condition associated with calciphylaxis, which comprise administering to a subject having a condition associated with calciphylaxis, a therapeutically effective amount of sodium thiosulfate provided herein. In one embodiment, the subject is a mammal. In another embodiment, the subject is a human.

In yet another embodiment, provided herein are methods for treating a dermatological disease or a condition associated with the skin, including, but not limited to, tinea versicolor, bacterial infection of the skin, mycotic infection of the skin, viral infection of the skin, mycotic infection of the nails, bacterial infection of the nails, viral infection of the nails, mycotic infection of the nailbeds, bacterial infection of the nailbeds, viral infection of the nailbeds, psoriasis, scleroderma, inflammation of the skin, inflammation of the nails, and inflammation of the nailbeds, which comprise administering to a subject having a dermatological disease or a condition associated with the skin, a therapeutically effective amount of sodium thiosulfate provided herein.

Depending on the condition, disorder, or disease, to be treated and the subject's condition, the sodium thiosulfate provided herein may be administered by oral, parenteral (e.g., intramuscular, intraperitoneal, intravenous, intracerebroventricular (ICV), intracistemal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 10 ng to about 1000 g, from about 10 mg to about 100 g, from about 500 mg to about 50 g, from about 1 g to about 25 g, or from about 5 g to about 12.5 g active ingredient(s) per dosage unit, and if the condition of the patient requires, the dose can, by way of alternative, be administered as a continuous infusion.

In certain embodiments, an appropriate dosage level is about 0.001 to about 100 g per kg patient body weight per day (g/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range the dosage may be about 0.01 to about 0.1, about 0.1 to about 1.0, about 1.0 to about 10, or about 10 to about 50 mg/kg per day.

6. Combination Therapy

The sodium thiosulfate provided herein may also be combined or used in combination with other therapeutic agents useful in the treatment and/or prevention of the diseases and conditions provided herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

As used herein, the term "synergistic" includes a combination of the sodium thiosulfate provided herein and another therapy (e.g., a prophylactic or therapeutic agent) which has been or is currently being used to treat, prevent, or manage a disease or disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The sodium thiosulfate provided herein can be administered in combination or alternation with another therapeutic agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The compounds provided herein can be administered in combination with other classes of compounds, including, but not limited to, vasodilators, such as sodium nitrite; keratolytic agents, such as salicylic acid; endothelin converting enzyme (ECE) inhibitors, such as phosphoramidon; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abciximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopeptidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; beta-adrenergic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, and vardenafil); protein tyrosine kinase inhibitors; antiinflammatories; antiproliferatives, such as methotrexate, FK506 (tacrolimus), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as paclitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathioprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

The sodium thiosulfate provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of the sodium thiosulfate provided herein.

In certain embodiments, the kit includes a container comprising a dosage form of the sodium thiosulfate provided herein, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); mmol (millimoles); eq. (equivalent); hr or hrs (hours); min (minutes).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Methodologies illustrated in the following examples are intended to exemplify the applicable chemistry through the use of specific examples and are not indicative of the scope of the disclosure.

Example 1

Preparation of Pharmaceutical Grade Sodium Thiosulfate Pentahydrate

Under nitrogen, 57 kilograms of sulfur and deionized water (799.1 kilograms) were charged to an inerted 500 gallon reactor system with an Orion Ross combination pH probe. The slurry was stirred and 161.4 kilograms of sodium sulfite was charged to the reactor. The reactor was heated to between 95 and 100° C. for 4 hours. The pH of the slurry within the reactor after 4 hours was 7.3. The reactor was cooled to 20+/−5° C. The pH of the cooled slurry was 6.6. 300 grams of sodium hydroxide 50 weight % solution was added to the reactor contents to increase the pH of the slurry within the reactor to 7.4. The contents of reactor were filtered through an Estrella filter. The resulting filtrate was distilled under vacuum at 50 to 100° C. to a specific gravity of 1.40. Maintaining the temperature of the solution at 50+/−5° C., 300 grams of activated carbon was added to the solution. The solution was stirred for one hour and 3 minutes and subsequently filtered with a bag filter and to remove the activated carbon. The filtered solution was cooled to 20+/−5° C. and 15 grams of sodium thiosulfate pentahydrate crystals were added to the solution. The solution was then cooled to 5+/−5° C. and stirred for 15 hours and 2 minutes. The contents within the reactor consisting of both solids and liquid were filtered through an Aurora filter under an inert environment. The mother liquor was used to rinse solids from the walls of the reactor. Solids were loaded onto drying trays and placed into a drying oven under full vacuum with a nitrogen bleed for 8 hours at 35° C. Drying continued after 8 hours until in-process testing confirmed that the water content (Loss on Drying) of the material was between 34.0 and 36.8%. The dried solid had a final mass of 112.5 kilograms (36% yield).

The analysis of sodium thiosulfate pentahydrate provided herein from the purification procedure is summarized in Table 1.

TABLE 1

| Analysis | Testing Result |
| --- | --- |
| USP Assay | 100% |
| HPIC Assay | 98.7 |
| Sodium | Complies$^a$ |
| Thiosulfate | Complies$^a$ |
| Reduction of Iodine TS to Iodide | Color was discharged |
| Water Content (Loss on Drying) | 36.4% |
| Calcium (Ca)-ammonium oxalate TS | No turbidity |
| Appearance | Colorless crystals |
| Odor | Odorless |
| Appearance of a 10% solution at 25° C. | Clear and colorless |
| pH of 10% solution at 25° C. | 6.6 |
| Heavy Metals | <10 ppm |
| Sulfide (as S) | <0.001% |
| Carbonate | 0.01% |
| Insoluble Matter | <0.005% |
| Chloride | 0.004% |
| Lead | <0.001% |
| Nitrogen Compounds (as N) | <0.002% |
| Sulfite | 0.01% |
| Sulfate (as $SO_4$) | 0.08% |
| Iron by ICP-OES or equivalent | 0.00019% |
| Calcium by ICP-OES or equivalent | None detected |
| Potassium by ICP-OES or equivalent | None detected |
| Organic volatile impurities | <300 ppm |

TABLE 1-continued

| Analysis | Testing Result |
| --- | --- |
| (Ethanol and Methanol) | ethanol; None detected - methanol |
| Total non-purgeable organic carbon or equivalent (NPOC) | <2.6 ppm |
| Mercury or ICP-OES or equivalent | None detected |
| Aluminum or ICP-OES or equivalent | 0.58 ppm |
| Arsenic or ICP-OES or equivalent | None detected |
| Selenium ICP-OES or equivalent | 0.000091% |
| Total Aerobic Microbial Count | <10 CFU/g |
| Total Yeast and Mold Count | <10 CFU/g |
| Bacterial Endotoxins | <0.0015 EU/mg |

<sup>a</sup>The identification of sodium and thiosulfate were determined using the identification tests, Method 191, as described in USP XXXII (2009).

Example 2

Method of Determining the Total Non-Purgeable Organic Carbon in Sodium Thiosulfate Pentahydrate Total non-purgeable organic carbon (NPOC) was determined using an InnovOx laboratory TOC Analyzer (GE Analytical Instruments, Inc., Boulder, Colo.). Water used for standard, reagent, and sample preparation had total organic carbon (TOC) of no greater than 0.10 ppm. Phosphoric acid was ACS reagent grade. Sodium persulfate was obtained from General Electric (GE Part # APK68050-01, Fairfield, Conn.). Sucrose USP was used as a reference standard. Compressed nitrogen has no greater than 1 ppm $CO_2$ and no greater than 1 ppm THC.

Phosphoric acid (6 N) used as acidification solution was prepared by adding approximately 100 mL of water to a 250 mL volumetric flask, followed by the slow addition of 100 mL of phosphoric acid and adding additional water to make the final volume of 250 mL. Phosphoric acid (6%) solution was prepared by adding 120 mL of 6N phosphoric acid solution to a 2,000 mL volumetric flask, and adding water to bring the volume to 100 mL at room temperature.

Sodium persulfate solution (30%) used as an oxidizer was prepared by adding 150 0.1 g of sodium persulfate to a 500 mL volumetric flask, and adding additional water to make the final volume of 500 mL, after the sodium persulfate was dissolved. The solution was allowed to sit for 3 days prior to use, and used within 14 days of the preparation.

The sucrose stock standard (250 ppm carbon based on 0.50 mg carbon/1.2 mg sucrose) was prepared by dissolving 9 mg of sucrose in 15 mL of water. TOC standard (10 ppm) was prepared by adding 4 mL of the sucrose stock standard to a 100 mL volumetric flask, followed by the addition of water to bring the volume to 100 mL at room temperature. TOC standard (2 ppm) was prepare by adding 10 mL of the 10 ppm TOC standard to a 50 mL volumetric flask, followed by the addition of water to bring the volume to 50 mL at room temperature. TOC standard (0.5 ppm) was prepare by adding 5 mL of the 10 ppm TOC standard to a 100 mL volumetric flask, followed by the addition of water to bring the volume to 100 mL at room temperature.

The sodium thiosulfate pentahydrate sample solution was prepared by adding 5.0 g of a sample into a 100 mL volumetric flask, followed by the addition of 6% phosphoric acid solution to bring the volume to 100 mL at room temperature. The sample solution was centrifuged for 15 min, and allowed to stand overnight to allow the precipitate to settle.

The InnovOx instrument was calibrated with 6% phosphoric acid solution (blank), and the 0.5 ppm, 2 ppm, and 10 ppm TOC standards, using the instrument parameters as shown in Table 2.

TABLE 2

| Protocol Name | Sodium Thiosulfate pentahydrate Cal |
| --- | --- |
| Number Points | 4 |
| Range | 0-1000 ppm |
| Acid | 0% |
| Oxidizer | 45.0% |
| Sparge | 4.0 min |
| Blank Correction | Off |
| Auto Dilution | Off |
| Cal Type | Pt-Pt |
| Replicates | 7 |
| Rejects | 2 |

The calibration curve requirements were that i) the correlation coefficient (r) of the average of the replicates must be no less than 0.99; ii) the RSD for the 2 and 10 ppm TOC standards must be no greater than 15%; iii) the limit of quantitation (LOQ) must be no greater than 3 ppm, which was calculated as follows:

$$LOQ=(10)(A)(B)/(C-D)$$

and iv) the limit of detection (LOD) must be no greater than 1 ppm, which was calculated as follows:

$$LOD=(3)(A)(B)/(C-D)$$

where:

A was the concentration of carbon in the 0.5 ppm TOC standard;

B was the standard deviation of the TOC concentration determined in the blank preparation;

C was the average TOC concentration determined in the 0.5 ppm TOC standard; and

D is the average TOC concentration determined in the blank preparation.

Samples were analyzed using the following instrument parameters as shown in Table 3.

TABLE 3

| Number Points | 4 |
| --- | --- |
| Range | 0-1000 ppm |
| Acid | 0% |
| Oxidizer | 45.0% |
| Sparge | 4.0 min |
| Flush | Dilution |
| Blank Correction | Off |
| Calibration | Sodium Thiosulfate Pentahydrate Cal |
| Replicates | 6 |
| Rejects | 2 |

The 2 ppm TOC standard was run before and after each sample analysis.

The system suitability requirements were that i) the RSD for the 2 ppm TOC standard must be no greater than 15%; ii) the percentage of theoretical response (% T) for the 2 ppm TOC standard determinations must be no less than 80% and no greater than 120%; which was calculated as follows:

$$\%T=100\times A/B;$$

where:

A was the result determined by the analyzer (ppm); and

B was the 2 ppm standard TOC concentration (ppm);

iii) for any sample that had a sample response at or above the LOQ to five times the LOQ, the RSD must be no greater than 25%; or for any sample that had a sample response more than five times the LOQ, the RSD must be no greater than 15%.

The total non-purgeable organic carbon in each sample was calculated as follows:

NPOC=$A \times B/C$;

where:
A was the result determined by the analyzer (ppm);
B was sample dilution volume (mL); and
C was sample mass (g).

In calculating total non-purgeable organic carbon, if A is less than the LOD, A in the formula was replaced with LOD for calculation to provide an upper limit for the total non-purgeable organic carbon value. If A is less than the LOQ, but more than the LOD, the total non-purgeable organic carbon value as calculated provided an approximate value and the LOQ set an upper limit for the total non-purgeable organic carbon.

Example 3

Method of Determining Sulfide Impurity in Sodium Thiosulfate Pentahydrate Drug Substance This protocol describes the procedure for qualification of a wet-chemistry test for detection of sulfide in sodium thiosulfate pentahydrate drug substance and drug product samples. The sulfide impurity, if present in samples, is detected as lead(II) sulfide, which forms gray precipitate. The method-detection-limit is set at 10 ppm or 10 µg/g of sulfide, based on the drug product concentration of 250 mg/mL sodium thiosulfate pentahydrate in solution, and use of 1 mL of drug product for testing.

a. Protocol

NaOH (0.01 N) reagent was prepared by dissolving approximately 4.0 g of sodium hydroxide (ACS reagent grade) in 1,000 mL of deionized water. The solution was further diluted from 10 mL to 100 mL volumetrically to yield 0.01 N sodium hydroxide solution. Alternatively, commercial 0.01 N sodium hydroxide may also be used.

Lead nitrate reagent (1 mg/mL) was prepared by accurately weighing 40±2 mg of lead nitrate (ACS reagent grade) and dissolving the lead nitrate in 25 mL of deionized water.

Sodium sulfide standard (50 mg/L sulfide) was prepared by accurately weighing 37±2 mg of sodium sulfide into a 100-mL volumetric flask. The sulfide was dissolved and diluted to the volume with 0.01 N sodium hydroxide.

For a sample, a 250 mg/mL solution in deionized water was prepared. Samples were tested singularly, in 10-mL test tubes or 4-mL glass vials with Teflon-lined caps. In parallel, test vials were prepared as shown in Table 4.

TABLE 4

| Sample Label | Deionized Water | Test Sample | Sulfide Standard | Pb(II) Reagent |
|---|---|---|---|---|
| Blank | 1.0 mL | None | 0.0 µL | 100 |
| Standard | 1.0 mL | None | 50 µL | 100 |
| Sample | None | 1.0 mL | 0.0 µL | 100 |
| Sample-Spike | None | 1.0 mL | 50 µL | 100 |

For quality control, the four test should meet the following requirements: i) the blank vial should be visibly clear and colorless; ii) the standard vial must have dark gray color or precipitate, clearly distinguishable from the blank; iii) the specificity solutions containing sulfate, sulfite, and chloride must have lighter gray color than the standard vial, and white precipitate is anticipated; and iv) the sulfide-spikes of specificity solutions containing sulfate, sulfite, and chloride must have darker gray color than the corresponding un-spiked solutions.

b. Method Specificity

The requirements for specificity were: i) the blank vial should be visibly clear and colorless; ii) the standard vial must have dark gray color or precipitate, clearly distinguishable from the blank; iii) the specificity solutions containing sulfate, sulfite, and chloride must have lighter gray color than the standard vial, and white precipitate is anticipated; and iv) the sulfide-spikes of specificity solutions containing sulfate, sulfite, and chloride must have darker gray color than the corresponding un-spiked solutions. All the requirements set forth in the protocol were met.

Test solutions were prepared to contain 1 mg/mL individually, of sodium sulfate, sodium sulfite, and sodium chloride. Duplicate vials of these solutions were tested to evaluate potential interference. In addition, these test solutions were individually test with sulfide spiking, in order to evaluate interference to sulfide detection. The results are summarized in Table 5. The sulfide standard was prepared at a concentration of 50 mg/L sulfide, and lead nitrate reagent was prepared at a concentration of 1 g/L (Pb(II)). The test solution color of gray or tan is accepted.

TABLE 5

Results for Method Specificity Test

| Test Solution | Vol. of Test Solution (mL) | Vol. of Sulfide Standard (µL) | Vol. of Lead(II) Reagent (µL) | Observations |
|---|---|---|---|---|
| Blank, Water | 1.0 | 0 | 100 | Clear colorless solution |
|  | 1.0 | 0 | 100 | Clear colorless solution |
| Sodium Sulfate | 1.0 | 0 | 100 | Clear colorless solution |
|  | 1.0 | 0 | 100 | Clear colorless solution |
| Sodium Sulfite | 1.0 | 0 | 100 | Slightly cloudy, white precipitate |
|  | 1.0 | 0 | 100 | Slightly cloudy, white precipitate |
| Sodium Chloride | 1.0 | 0 | 100 | Clear colorless solution |

TABLE 5-continued

Results for Method Specificity Test

| Test Solution | Vol. of Test Solution (mL) | Vol. of Sulfide Standard (μL) | Vol. of Lead(II) Reagent (μL) | Observations |
|---|---|---|---|---|
| | 1.0 | 0 | 100 | Clear colorless solution |
| Standard (blank-Spike) | 1.0 | 50 | 100 | Clear tan solution |
| Sodium Sulfate-Spike | 1.0 | 50 | 100 | Light tan solution, darker particulate |
| Sodium Sulfite-Spike | 1.0 | 50 | 100 | Slightly cloudy tan solution, dark particulate |
| Sodium Chloride-Spike | 1.0 | 50 | 100 | Light tan solution |

The test method was shown to be specific to sulfide in the presence of sulfate, sulfite, and chloride.

c. Limit of Detection

As shown in Tables 6 and 7, the presence of sulfide in the blank (water) or in the drug product sample (sodium thiosulfate pentahydrate) was determined at 4 ppm and above with detection of tan color. According to the protocol, the limit of detection of sulfide in sodium thiosulfate pentahydrate drug product was determined to be 4 ppm.

The limit of detection was determined to be 4 ppm, which was well below the limit (10 ppm).

TABLE 6

| Sample Label | Vol. of Deionized Water | Vol. of Sample | Vol. of Sulfide Standard | Vol. of Lead (II) Reagent | Observations |
|---|---|---|---|---|---|
| Sample-blank | 1.0 mL | 0 | 0 μL | 100 μL | Clear colorless solution |
| 2 ppm Standard | 1.0 mL | 0 | 10 μL | 100 μL | Clear, maybe hint of tan |
| 4 ppm Standard | 1.0 mL | 0 | 20 μL | 100 μL | Clear solution, light tan color |
| 5 ppm Standard | 1.0 mL | 0 | 30 μL | 100 μL | Clear solution, tan color |
| 8 ppm Standard | 1.0 mL | 0 | 40 μL | 100 μL | Clear solution, tan color |
| 10 ppm Standard | 1.0 mL | 0 | 50 μL | 100 μL | Clear solution, tan color |
| Sample-blank | 0 | 1.0 mL | 0 μL | 100 μL | Clear colorless solution |
| 2 ppm Standard | 0 | 1.0 mL | 10 μL | 100 μL | Clear colorless solution |
| 4 ppm Standard | 0 | 1.0 mL | 20 μL | 100 μL | Clear solution, light tan color |
| 5 ppm Standard | 0 | 1.0 mL | 30 μL | 100 μL | Clear solution, tan color |
| 8 ppm Standard | 0 | 1.0 mL | 40 μL | 100 μL | Clear solution, tan color |
| 10 ppm Standard | 0 | 1.0 mL | 50 μL | 100 μL | Clear solution, tan color |

TABLE 7

| Sample Label | Vol. of Deionized Water | Vol. of Sample | Vol. of Sulfide Standard | Vol. of Lead (II) Reagent | Observations |
|---|---|---|---|---|---|
| Sample-blank | 1.0 mL | 0 | 0 μL | 100 μL | Clear colorless solution |
| 2 ppm Standard | 1.0 mL | 0 | 10 μL | 100 μL | Clear solution, very light color |
| 4 ppm Standard | 1.0 mL | 0 | 20 μL | 100 μL | Clear solution, light tan color |
| 5 ppm Standard | 1.0 mL | 0 | 30 μL | 100 μL | Clear solution, light tan color |
| 8 ppm Standard | 1.0 mL | 0 | 40 μL | 100 μL | Clear solution, tan color |
| 10 ppm Standard | 1.0 mL | 0 | 50 μL | 100 μL | Clear solution, tan color |
| Sample-blank | 0 | 1.0 mL | 0 μL | 100 μL | Clear colorless solution |
| 2 ppm Standard | 0 | 1.0 mL | 10 μL | 100 μL | Clear solution, very light color |
| 4 ppm Standard | 0 | 1.0 mL | 20 μL | 100 μL | Clear solution, light tan color |
| 5 ppm Standard | 0 | 1.0 mL | 30 μL | 100 μL | Clear solution, light tan color |
| 8 ppm Standard | 0 | 1.0 mL | 40 μL | 100 μL | Clear solution, tan color |
| 10 ppm Standard | 0 | 1.0 mL | 50 μL | 100 μL | Clear solution, tan color |

Example 4

Method for Determination of Thiosulfate in Sodium Thiosulfate Pentahydrate

The concentration of sodium thiosulfate pentahydrate in a drug product was determined using ion chromatography with electrochemical conductivity detection on a Dionex IonPac AS12A analytical column (P/N 046034, Dionex Corporation, Sunnyvale, Calif.), eluted with 13.5 mM sodium carbonate (ACS reagent grade) and 1.5 mM sodium bicarbonate (ACS reagent grade) in deionized water at 1.5 mL/min with a detector range of 50 μS for 15 min. The ion-exchange column was run at room temperature with suppressor current at 100 mA.

For mobile phase preparation, a stock sodium carbonate solution (500 mM) was prepared by adding 26.5 g of sodium carbonate (ACS reagent grade) to a 500 mL volumetric flask, followed by the addition of deionized water to bring the volume to 500 mL at room temperature; and a stock sodium bicarbonate solution (500 mM) was prepared by adding 10.5 g of sodium bicarbonate (ACS reagent grade) to a 500 mL volumetric flask, followed by the addition of deionized water to bring the volume to 500 mL at room temperature A mobile phase was prepared by adding 54 mL stock sodium carbonate solution and 6 mL stock sodium bicarbonate solution to a 2 L volumetric flask, followed by the addition of deionized water to bring the volume to 2 L at room temperature.

A stock sodium thiosulfate standard solution (1 g/L) was prepared by adding 0.10 g of sodium thiosulfate pentahydrate to a 100 mL volumetric flask, followed by the addition of deionized water to bring the volume to 100 mL at room temperature. A sodium thiosulfate reference standard was prepared by adding 10.0 mL of the stock sodium thiosulfate solution to a 100 mL volumetric flask, followed by the addition of deionized water to bring the volume to 100 mL at room temperature. A linearity standard was prepared by diluting the sodium thiosulfate reference standard (12.5 mL) to 25.0 mL with deionized water.

Thiosulfate-containing samples were prepared in duplicate. First, a stock sample solution was prepared by adding 2.0 mL of the sample to a 100 mL volumetric flask, followed by the addition of deionized water to bring the volume to 100 mL at room temperature.

System suitability was determined by first injecting the sodium thiosulfate reference standard, followed by an injection of deionized water, to ensure no carryover that may interfere with the analysis. The sodium thiosulfate reference standard was then injected six times. The percent relative standard deviation (% RSD) of the peak area of thiosulfate was calculated. The first injection was used to calculate the tailing factor and number of theoretical plates according to Method 621 USP XXXII (2009). The % RSD of the peak area for the initial six injections of the thiosulfate peak must be NMT 2.0%. The tailing factor for the thiosulfate peak must be NMT 2.0. The number of theoretical plates (N) for the thiosulfate must be NLT 3,000. The area % RSD for the six injections plus each continuing calibration injections must be NMT 3.0%.

The sodium thiosulfate reference standard was injected twice and the area difference (%) between the duplicate injections was determined. The % difference between the duplicate injections should be NMT 2.0% and the error of the assay value must be NMT 2.0%. The average area response thus determined was used to calculate the concentration of the previous six injections, and the difference in percentage of the concentration thus determined from the actual concentration was determined.

The sample solution diluent was injected once to check carryover and other peaks arising from the diluent. The peak area response at the retention time of thiosulfate should be NMT 1% of the area response for the sodium thiosulfate reference standard.

Linearity standard was injected twice. For the linearity standard, the average peak area must be between 47.0 and 53.0% of the average peak area for the system suitability injections. For the linearity standard, the % difference between the duplication injections must be NMT 2.0%.

Each sample solution was injected in duplicate. The % difference between the duplicate was calculated. The % difference between in sodium thiosulfate assay concentrations between the duplicate preparations was also calculated.

The instrument was verified every six sample injections and after the final sample injection by reanalyzing the sodium thiosulfate reference standard in duplicate. For each sample, the % difference between the duplication injections must be NMT 2.0%, and the % difference between the assay concentrations of thiosulfate in duplicate preparations must be NMT 2%. The concentration of a sodium thiosulfate pentahydrate sample was calculated based on its peak area in comparison with that of the sodium thiosulfate standard.

Example 5

Determination of Trace Levels of Carbonate in Sodium Thiosulfate Pentahydrate

All glassware was thoroughly rinsed with deionized water at least three times. Glassware used for weighing can be oven-dried, and extreme were taken when handling as not to contaminate the glassware with organic matter. Glassware used for dilution only was pre-rinsed at least three times with acidific reagent water, which was prepared by adding approximately 1 to 2 mL of concentrated phosphoric acid to 4,000 mL deionized water, followed by thoroughly rinsing with deionized water just prior to use. When weighing, a sterile plastic spatula was used instead of a metal spatula to reduce potential contamination.

Sodium carbonate stock solution used for preparing carbonate standards was prepared by dissolving 0.177 g of sodium carbonate (ACS reagent grade) in 100.0 mL deionized water. Nominal concentration of carbonate is 1,000 mg/L, equivalent to 200 mg/L of carbon. A series of carbonate calibration standards was prepared by pipetting 100, 200, 400, 800, and 1,000 µL of sodium carbonate stock solution into separate 200 mL volumetric flasks, followed by adding deionized water to bring the volume to 200 mL at room temperature. Nominal concentrations are 0.5, 1.0, 2.0, 4.0, and 5.0 mg/L of carbonate, respectively. Care was taken to make sure all carbonate solutions were tightly sealed and stored in a cool area away from excessive heat.

Samples were prepared by weighing accurately to the nearest 0.01 mg and transferring an amount of the sample equivalent to less than 1.0 mg/L of carbon (5.0 mg/L carbonate) into a 100 mL volumetric flask. For a sodium thiosulfate pentahydrate drug substance with limit of carbonate at <0.01%, 1.00 g of the sample in 100 mL water would yield 1 mg/L of carbonate, equivalent to 0.2 mg/L carbon, when presented at 0.01%. Then, 20 mL of deionized was added to the 100 mL volumetric flask to dissolve the sample. The sample solution was titrated with 0.1 N iodine VS (approximately 40 mL) (cat. #318981, Sigma-Aldrich, St. Louis, Mo.) until a persistent yellow color is observed. Deionized water was added to bring the volume to 100 mL at room temperature.

Total inorganic carbon, was determined using a Shimadzu TOC-V Analyzer in IC mode. In the IC mode, the sample was acidified in line with phosphoric acid to convert the inorganic carbon (carbonate and bicarbonate) to carbon dioxide, which was then routed to the non-dispersive infrared detector for quantitation. Only pre-cleaned TOC vials were used on the analyzer and each vial was filled completely with either standards or samples and left leave no head space in the vial. The vials were secured with caps.

Under standard set-up, three measurements were made for each vial (standard, sample, or blank). Three measurements constituted a single run. Three rums of blank (deionized water) were performed to ensure that the analyzer was equilibrated and the results were consistent.

One run of each calibration standards was performed. The % RSD and average area response from the three injections of each standard were determined. Linear regression of the average areas versus the standard concentrations was performed to determine the slope, intercept, and correlation coefficient for the calibration standards. Blank was included in the linear regression analysis, but no forcing through zero. One run was performed for each sample. The % RSD of the three injections and the average peak area was determined, from which the carbonate concentration was calculated based on the calibration standards.

The analyzer was calibrated every six sample runs and after the final sample injection by performing one run of blank, followed by one run of the 2.0 mg/L calibration standard. The % RSD of both and carbonate recovery from the calibration standard curve were calculated.

For quality control, the area (response) % RSD of the three injections for each standard must be no greater than (NMT) 10%. The calibration curve for carbonate must have a correlation coefficient of no less than (NLT) 0.995. The area % RSD of the initial blank and continuing calibration blank injections must be no greater than (NMT) 15%. The area % RSD for continuing calibration standard (2.0 mg/L) injections must be not more than (NMT) 10%. The % Recovery of the 2.0 mg/L continuing calibration standard must be 85% to 115%.

The percent relative standard deviation (% RSD) is the standard deviation divided by the mean times 100.

Example 6

Pharmaceutical Formulation Comprising Sodium Thiosulfate Pentahydrate

An illustrative injection, solution comprising pharmaceutical grade sodium thiosulfate pentahydrate is set forth in Table 8.

TABLE 8

| Ingredient | Function | Unit Formulation (per mL) | Unit Formulation (per 50 mL vial) |
|---|---|---|---|
| Pharmaceutical grade Sodium thiosulfate, USP | Active pharmaceutical ingredient | 250.0 mg | 12.5 g |
| Potassium chloride, USP | Tonicity modifying agent | 4.40 mg | 220 mg |
| Boric acid, NF | Buffer | 2.80 mg | 140 mg |
| Boric acid, NF | pH adjustment | qs to target pH | qs to target pH |
| Sodium hydroxide, NF | pH adjustment | qs to target pH | qs to target pH |
| WFI, USP | Solvent | qs | Qs |

Abbreviations: NF, National Formulary; qs, quantity sufficient; USP, United States Pharmacopeia; WFI, water for injection.

* * * * *

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. Pharmaceutical grade sodium thiosulfate pentahydrate which contains no greater than about 8 ppm of non-purgeable organic carbon, contains no greater than about 0.05 ppm of mercury, contains no greater than about 2 ppm of aluminum, contains no greater than about 0.003% by weight of selenium, contains no less than about 98% by weight and no greater than about 102% by weight of sodium thiosulfate on an anhydrous basis measured by ion chromatography, has a water content between 32% and 37% by weight, has a heavy metal content of no greater than about 10 ppm, contains no greater than about 200 ppm of chloride, contains no greater than about 0.001% by weight of sulfide, contains no greater than about 0.002% by weight of iron, contains no greater than about 0.01% by weight of calcium, contains no greater than about 0.005% by weight of potassium, contains no greater than about 0.1% of sulfite, contains no greater than about 0.5% of sulfate, contains no greater than about 3 ppm of arsenic, contains no greater than about 0.001% by weight of lead, has total aerobic count of microbial load of no greater than about 100 CFU/g, has total yeast and mold count of no greater than about 20 CFU/g, contains no greater than about 0.02 EU/mg of bacterial endotoxins, contains no greater than about 0.002% by weight of nitrogen compounds, contains no greater than about 0.005% by weight of insoluble matter, contains no greater than 0.01% by weight of residual anti-caking agent, and contains no greater than ICH Q3C (R3) limits of organic volatile impurities, wherein a 10% aqueous solution of the solid sodium thiosulfate pentahydrate at 25° C. is colorless and has a pH between about 6.0 and about 8.0, and wherein the solid sodium thiosulfate pentahydrate is odorless crystals.

2. The pharmaceutical grade sodium thiosulfate pentahydrate of claim 1, which has a positive identification test for sodium.

3. The pharmaceutical grade sodium thiosulfate pentahydrate of claim 1, which has a positive identification test for thiosulfate.

4. A pharmaceutical composition comprising sodium thiosulfate pentahydrate and one or more pharmaceutically acceptable carriers or excipients, wherein the sodium thiosulfate pentahydrate contains no greater than about 8 ppm of non-purgeable organic carbon, contains no greater than about 0.05 ppm of mercury, contains no greater than about 2 ppm of aluminum, contains no greater than about 0.003% by weight of selenium, contains no less than about 98% by weight and no greater than about 102% by weight of sodium thiosulfate on an anhydrous basis measured by ion chromatography, has a water content between 32% and 37% by weight, has a heavy metal content of no greater than about 10 ppm, contains no greater than about 200 ppm of chloride, contains no greater than about 0.001% by weight of sulfide, contains no greater than about 0.002% by weight of iron, contains no greater than about 0.01% by weight of calcium, contains no greater than about 0.005% by weight of potassium, contains no greater than about 0.1% of sulfite, contains no greater than about 0.5% of sulfate, contains no greater than about 3 ppm of arsenic, contains no greater than about 0.001% by weight of lead, has total aerobic count of microbial load of no greater than about 100 CFU/g, has total yeast and mold count of no greater than about 20 CFU/g, contains no greater than about 0.02 EU/mg of bacterial endotoxins, contains no greater than about 0.002% by weight of nitrogen compounds, contains no greater than about 0.005% by weight of insoluble matter, contains no greater than 0.01% by weight of residual anti-caking agent, and contains no greater than ICH Q3C (R3) limits of organic volatile impurities.

5. The pharmaceutical composition of claim 4, wherein the composition is formulated for oral, parenteral, inhalation, nasal, intravesical, vaginal, rectal, sublingual, ophthalmic, or topical administration.

6. The pharmaceutical composition of claim 5, wherein the composition is formulated as a single dosage form.

7. The pharmaceutical composition of any of claim 4, wherein the pharmaceutically acceptable excipient is water.

8. The pharmaceutical composition of claim 4, further comprising an isotonic agent and one or more pH adjusting agents.

9. The pharmaceutical composition of claim 8 which is sterile and suitable for intravenous administration, wherein the isotonic agent is potassium chloride, present at about 4.40 mg/mL and the pH adjusting agents are boric acid, present at about 2.80 mg/mL and sodium hydroxide, wherein the sodium thiosulfate pentahydrate is present at about 250.0 mg/mL.

10. A sterile, aqueous solution suitable for intravenous injection, comprising 250.0 mg/mL sodium thiosulfate pentahydrate of claim 1, 4.40 mg/mL potassium chloride, and 2.80 mg/mL boric acid.

11. The sterile, aqueous solution of claim 10, further comprising an additional quantity of boric acid and sodium hydroxide sufficient to achieve a pH suitable for injection.

12. The sterile, aqueous solution of claim 10, comprising 12.5grams of said sodium thiosulfate pentahydrate, 140 mg boric acid and 220 mg potassium chloride.

13. A sterile, aqueous solution intended for intravenous injection prepared by combining the sodium thiosulfate pentahydrate of claim 1, boric acid, potassium chloride, sodium hydroxide and water.

14. A method for treating platinum-induced ototoxicity, platinum-induced nephrotoxicity, cyanide poisoning, calciphylaxis, vascular calcification associated with atherosclerosis or a fungal infection of the skin, nailbeds, or nails, comprising administering to a subject in need thereof a therapeutically effective amount of pharmaceutical grade sodium thiosulfate pentahydrate of claim 1.

15. The method of claim 14, wherein said subject is treated for cyanide poisoning.

* * * * *